(12) United States Patent
Nakata et al.

(10) Patent No.: US 9,134,279 B2
(45) Date of Patent: Sep. 15, 2015

(54) INTERNAL DEFECT INSPECTION METHOD AND APPARATUS FOR THE SAME

(75) Inventors: Toshihiko Nakata, Hiratsuka (JP); Tetsuya Matsui, Hitachi (JP); Takehiro Tachizaki, Yokohama (JP); Kazushi Yoshimura, Kamakura (JP); Masahiro Watanabe, Yokohama (JP)

(73) Assignee: HITACHI, LTD., Tokyo (JP)

( * ) Notice: Subject to any disclaimer, the term of this patent is extended or adjusted under 35 U.S.C. 154(b) by 290 days.

(21) Appl. No.: 13/819,355

(22) PCT Filed: Jun. 1, 2011

(86) PCT No.: PCT/JP2011/003072
§ 371 (c)(1),
(2), (4) Date: Feb. 27, 2013

(87) PCT Pub. No.: WO2012/026054
PCT Pub. Date: Mar. 1, 2012

(65) Prior Publication Data
US 2013/0160552 A1     Jun. 27, 2013

(30) Foreign Application Priority Data

Aug. 27, 2010   (JP) ................................. 2010-190253

(51) Int. Cl.
*G01N 29/04*   (2006.01)
*G01N 29/22*   (2006.01)
(Continued)

(52) U.S. Cl.
CPC .............. *G01N 29/221* (2013.01); *G01N 29/04* (2013.01); *G01N 29/043* (2013.01); *G01N 29/0654* (2013.01); *G01N 29/2418* (2013.01)

(58) Field of Classification Search
CPC .............. G01N 21/1702; G01N 21/67; G01N 21/1717; G01N 29/2431; G01N 29/2418; G01N 29/07; G01N 29/228; G01N 29/04; G01N 29/2412; G01N 29/265; G01N 29/043; G01N 29/046; G01N 29/343; G01N 29/40; G01N 29/42; G01N 29/2487; G01N 29/262
USPC ........... 73/596–599, 632, 643, 618–621, 602, 73/627–629
See application file for complete search history.

(56) References Cited

U.S. PATENT DOCUMENTS 4,137,778 A  *  2/1979  Primbsch ........................ 73/627
4,633,715 A  *  1/1987  Monchalin ..................... 73/657
(Continued)

FOREIGN PATENT DOCUMENTS

JP       61-169759 A       7/1986
JP       05-288720          11/1993
(Continued)

OTHER PUBLICATIONS

Donald E. Yuhas et al., NDE of Electronic Components, ASNT Natl. Conf.., Spring 1980. pp. 11-17, Sonoscan, Inc., Bensenville, IL.
(Continued)

*Primary Examiner* — Helen Kwok
(74) *Attorney, Agent, or Firm* — Baker Botts L.L.P.

(57) ABSTRACT

An internal defect inspection method where an ultrasonic wave is emitted from an ultrasonic wave transmitter toward a sample, the ultrasonic wave reflected by the sample is detected by an imaging type common-path interferometer as an interference signal, an ultrasonic wave signal is obtained from the interference signal, and any defect within the sample is detected from the ultrasonic wave signal. An internal defect inspection apparatus including an ultrasonic wave transmitter, an imaging type common-path interferometer and an ultrasonic wave signal detecting device is also provided.

14 Claims, 10 Drawing Sheets

(51) Int. Cl.
*G01N 29/24* (2006.01)
*G01N 29/06* (2006.01)

(56) References Cited

U.S. PATENT DOCUMENTS

| | | | |
|---|---|---|---|
| 5,062,715 | A * | 11/1991 | Nakata et al. ............... 356/432 |
| 5,781,294 | A * | 7/1998 | Nakata et al. ............... 356/487 |
| 6,382,028 | B1 * | 5/2002 | Wooh et al. .................. 73/602 |
| 2001/0015104 | A1 * | 8/2001 | Wooh .......................... 73/598 |
| 2004/0092808 | A1 * | 5/2004 | Ogawa ....................... 600/407 |
| 2004/0154402 | A1 * | 8/2004 | Drake, Jr. .................... 73/621 |
| 2005/0210985 | A1 * | 9/2005 | Pepper et al. ................ 73/643 |
| 2007/0157730 | A1 * | 7/2007 | Ochiai et al. ................ 73/627 |
| 2008/0291465 | A1 * | 11/2008 | Lorraine et al. ............. 356/502 |
| 2008/0302187 | A1 * | 12/2008 | Huber et al. ................. 73/597 |
| 2009/0073457 | A1 * | 3/2009 | Nakata et al. ............... 356/498 |
| 2012/0067128 | A1 * | 3/2012 | Oberhoff et al. ............. 73/632 |
| 2012/0274931 | A1 * | 11/2012 | Otani et al. ............... 356/237.3 |

FOREIGN PATENT DOCUMENTS

| | | |
|---|---|---|
| JP | 08-285821 | 11/1996 |
| JP | 9-318603 | 12/1997 |
| JP | 2003-329652 A | 11/2003 |
| JP | 2004-89310 | 3/2004 |
| JP | 2007-46938 | 2/2007 |
| JP | 2008-286518 | 11/2008 |
| JP | 2009-150692 | 7/2009 |

OTHER PUBLICATIONS

P. Cielo et al., Laser Generation of Convergent Acoustic Waves and Applications to Materials Evaluation, IEEE 1986, Ultrasonics Symposium, pp. 515-526.

Toshihiko Nakata et al., Real-time photodisplacement microscope for high-sensitivity simultaneous surface and subsurface inspection, Applied Optics, Apr. 20, 2006, pp. 2643-2655, vol. 45, No. 12.

Office Action, mailed Jul. 21, 2015, which issued during the prosecution of Japanese Patent Application No. 2010-190253, which corresponds to the present application.

* cited by examiner

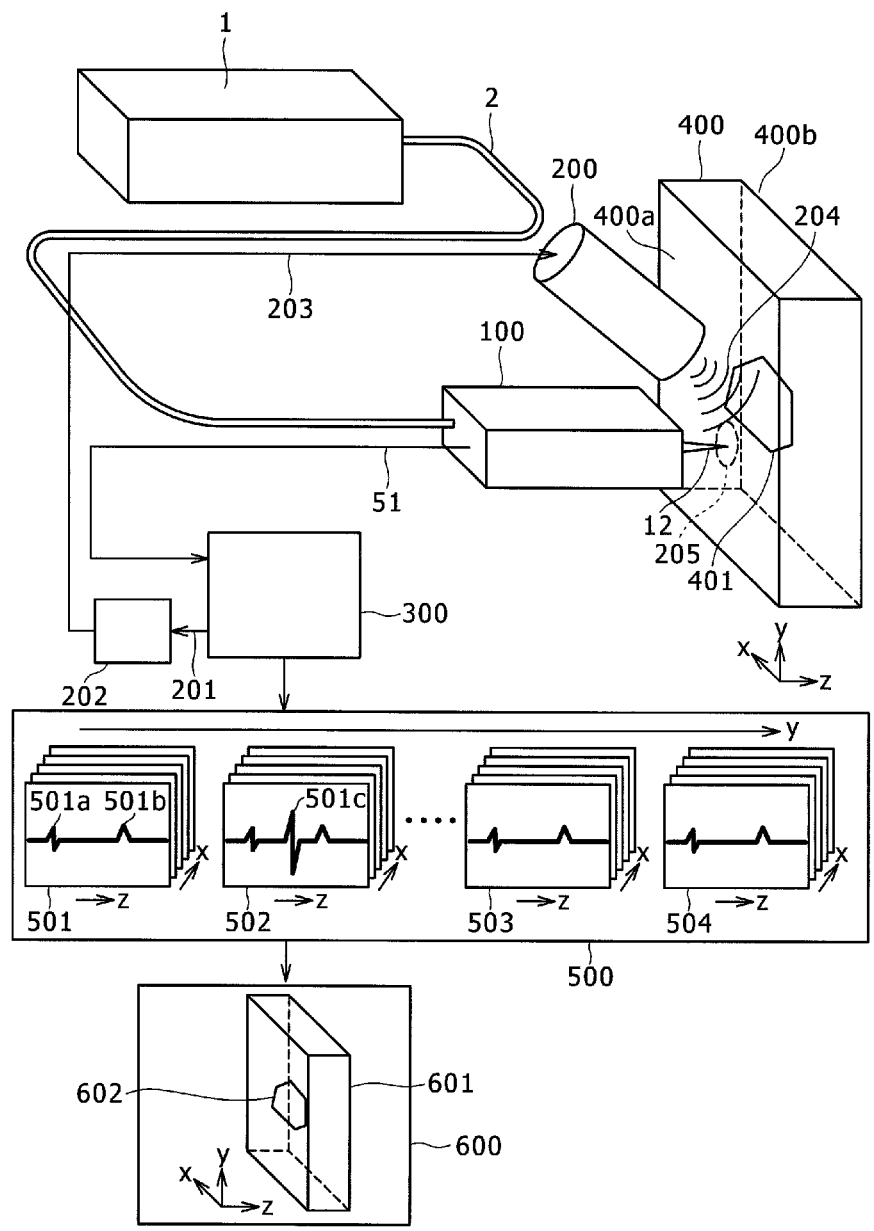

F I G . 1 1
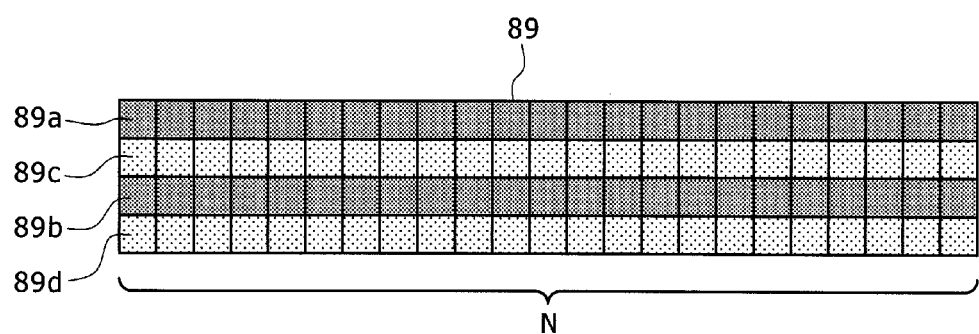

INTERNAL DEFECT INSPECTION METHOD AND APPARATUS FOR THE SAME

TECHNICAL FIELD

The present invention relates to an internal defect inspection method and an apparatus for the same, and more particularly to an internal defect inspection method and an apparatus for the same by which an airborne ultrasonic wave is used to propagate an ultrasonic wave within a sample and an ultrasonic wave vibration reflected or transmitted by any internal defect is detected with an optical interferometer.

Known methods for inspecting a sample for any internal defect include one using a scanning laser acoustic microscope (SLAM) by which, as disclosed in Non-patent Document 1 (ASNT Natl. Conf., Spring 1980, pp. 11-17 (1980)), an ultrasonic wave excited in a solid sample with water as a coupler and reflected or transmitted by any defect within the sample is detected with an optical interferometer.

Further, Non-patent Document 2 (Proceedings of 1986 IEEE ULTRASONICS SYMPOSIUM, pp. 515-526 (1986)) discloses a method by which a solid sample is irradiated with a pulse laser beam to excite an elastic wave in the sample, and variations in amplitude and phase of the surface elastic wave caused by any defect within the sample are detected with an optical interferometer.

Further, Non-patent Document 3 (Applied Optics, 45, pp. 2643-2655 (2006)) discloses a method by which a solid sample is irradiated with a linear intensity-modulated laser beam and an internal defect image is formulated at high speed by collectively detecting the amplitude and phase of any minute thermal displacement on the sample surface with an optical interferometer using a linear beam.

Further, Patent Document 1 (Japanese Unexamined Patent Application Publication No. 2009-150692) discloses a method by which an airborne ultrasonic wave is propagated within a sample and an airborne ultrasonic wave from any internal defect is detected.

Also, there is known a method by which an ultrasonic probe is brought into tight contact with the surface of a sample and excitation and detection of an ultrasonic wave is accomplished.

SUMMARY

However, the use of a SLAM according to Non-patent Document 1 by which an ultrasonic wave excited in a solid sample with water as a coupler involves the risk of contaminating the sample with water and therefore limited in the range of applicability. It involves another problem that a conventional optical interferometer is insufficient in measurement sensitivity, ranging from the nm to sub-μm order, and accordingly no adequate sensitivity for detecting internal defects is available.

Also, the method of irradiating a solid sample with a pulse laser beam to excite an elastic wave in the sample according to Non-patent Document 2 involves the similar problem that the optical interferometer is insufficient in measurement sensitivity, ranging from the nm to sub-μm order, and accordingly the laser output should inevitably be increased, giving rise to ablation or the like and damaging the sample.

Further, the collective imaging method according to Non-patent Document 3 by which a solid sample is irradiated with a linear intensity-modulated laser beam and the amplitude and phase of minute thermal displacement on the sample surface are collectively imaged by an optical interferometer using a linear beam involves the similar problem that the optical interferometer is insufficient in measurement sensitivity, ranging from the nm to sub-μm order, and no sufficient sensitivity for internal defect detection can be obtained.

Also, the method according to Patent Document 1 by which an airborne ultrasonic wave is propagated within a sample and an airborne ultrasonic wave from any internal defect is detected involves a problem that no sufficient sensitivity for internal defect detection can be obtained because the ultrasonic wave propagated within the sample is weak and moreover the airborne ultrasonic wave from the defect is also extremely weak.

Further, in a case where convexes and concaves are present on the sample surface or the sample surface is a rough face, it is impossible to bring an ultrasonic waves probe into tight contact with the surface of a sample and the sensitivity for internal defect detection is significantly reduced.

Therefore, in view of the problems cited above, the present invention is intended to provide an internal defect inspection method and an apparatus for implementing the method by which an ultrasonic wave is excited in a sample without contact with the sample and accordingly without damaging the sample, and an ultrasonic wave from any internal defect of the sample is detected without being affected by the sample surface, in a non-contact state and with high sensitivity.

The invention provides an internal defect inspection method by which an ultrasonic wave is emitted from an ultrasonic wave transmitter toward a sample, an ultrasonic wave reflected by the sample is detected as an interference signal with an imaging type common-path interferometer, an ultrasonic wave signal is obtained from the interference signal, and any defect within the sample is detected from the ultrasonic wave signal.

In another aspect, the invention provides an internal defect inspection apparatus comprising an ultrasonic wave transmitter that emits an ultrasonic wave into the air to be propagated within a sample, an imaging type common-path interferometer that detects on the sample surface the ultrasonic wave propagating within the sample as an ultrasonic wave vibration, and an ultrasonic wave signal detector that detects an ultrasonic wave signal from the interference signal detected by the imaging type common-path interferometer.

According to the invention, it is possible to provide an internal defect inspection method and an apparatus for exciting an ultrasonic wave in a sample without contact with the sample and accordingly without damaging the sample and detecting an ultrasonic wave from any internal defect of the sample without being affected by the sample surface in a non-contact state and with high sensitivity.

BRIEF DESCRIPTION OF THE DRAWINGS

FIG. 1 is a combination of a perspective view and a block diagram showing the overall configuration of an internal defect inspection apparatus in a first embodiment of the present invention;

FIG. 11 shows a front view of the photo acceptance face of a divided type photoelectric conversion element in the fourth embodiment of the invention.

DETAILED DESCRIPTION

First Embodiment

Figure 2:
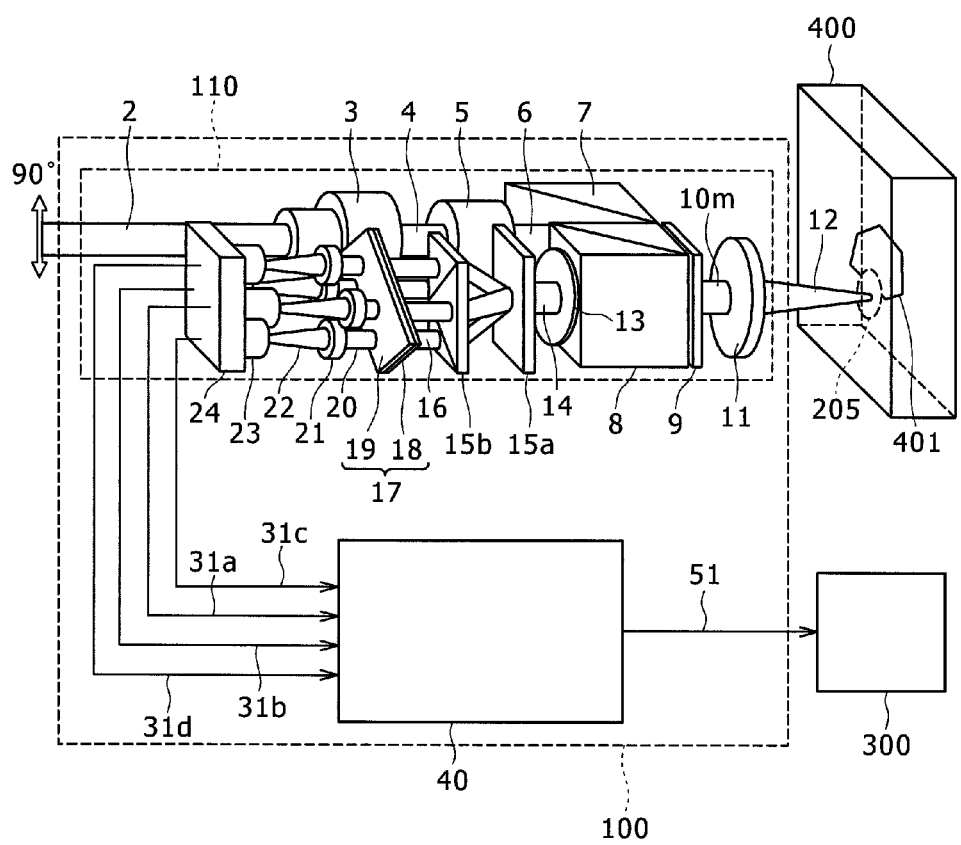
FIG. 2 is a combination of a perspective view and a block diagram showing the configuration of an interferometric displacement sensor in the first embodiment of the invention.

A first embodiment of the present invention will be described below with reference to FIG. 1 through FIG. 5. FIG. 1 shows an overall configuration of an internal defect inspection apparatus in the first embodiment. This internal defect inspection apparatus comprises an ultrasonic wave transmitting unit 200 that emits an airborne ultrasonic wave, an interferometric displacement sensor 100 that detects an ultrasonic wave vibration that is reflected or transmitted from within a sample, a laser source unit 1, a polarization maintaining fiber 2 that guides a laser beam emitted from the laser source unit 1 to the interferometric displacement sensor 100, a signal controller-processor 300 that executes control of airborne ultrasonic wave emission, analysis and processing of the amplitude and phase of the detected ultrasonic wave, and control of the ultrasonic wave image configuration, a three-dimensional image constructing unit 500 that constructs from detected ultrasonic wave signals a three-dimensional ultrasonic wave image regarding the positions of the sample in the x direction, y direction and z direction, and a display with defect determining unit 600 that displays the three-dimensional ultrasonic wave image and executes defect determination.

A pulse signal 203 or a continuous wave signal 203 is outputted from a transmitter 202 on the basis of a control signal 201 from the signal controller-processor 300, and an airborne ultrasonic wave 204 is emitted from the ultrasonic wave transmitting unit 200. The ultrasonic wave transmitting unit 200 is provided with an oscillator that is caused to oscillate by the application of a voltage and emits an ultrasonic wave and an acoustic matching layer, and the equipment of the oscillator with the acoustic matching layer restrains the difference in acoustic impedance between the oscillator and air to enable the ultrasonic wave to propagate in the air. As the oscillator, usually a piezoelectric element is used, and as the acoustic matching layer, clay, epoxy, polyurethane or the like, whose difference in acoustic impedance is small both for the piezoelectric element and air, is used. The airborne ultrasonic wave 204 propagates inward from the surface of a sample 400 of a rolled steel sheet, composite steel sheet, casting, ceramic substrate or the like, and is reflected by a defect 401 having arisen inside the sample, such as an exfoliation, crack or void. This reflected ultrasonic wave, though attenuating, excites a weak ultrasonic wave vibration 205 on the surface of the sample 400.

A linearly polarized laser beam emitted from the laser source unit 1 configured of a He—Ne laser of 632.8 nm in wavelength or a solid laser of 532 nm in wavelength is guided by the polarization maintaining fiber 2 to the interferometric displacement sensor 100. A probe beam 12 emitted from the interferometric displacement sensor 100 irradiates the excitation area where the ultrasonic wave vibration 205 is generated, and a phase change accompanying the ultrasonic wave vibration occurs on its reflected beam. This phase change is detected by the interferometric displacement sensor 100 as an amplitude change of an interference beam, and outputted as an ultrasonic wave signal 51.

The ultrasonic wave signal 51 is sent to the three-dimensional image constructing unit 500 via the signal controller-processor 300. In the three-dimensional image constructing unit 500, a three-dimensional ultrasonic wave image representing the internal structure of the sample 400 is constructed by the use of ultrasonic wave image sets 501 to 504 obtained by scanning the ultrasonic wave transmitting unit 200 and the interferometric displacement sensor 100 in the x and y directions at a certain distance in the air over the sample 400. Thus, the ultrasonic wave image set 501 is a plurality of sheets of time axis signal (z-directional signal) data collected while scanning the ultrasonic wave transmitting unit 200 and the interferometric displacement sensor 100 in the x direction, and corresponds to a two-dimensional ultrasonic wave image regarding the x direction and the z direction. By further executing this operation while scanning the ultrasonic wave transmitting unit 200 and the interferometric displacement sensor 100 in the y direction to repeat acquisition of the ultrasonic wave image sets 502, 503, 504, . . . , a three-dimensional ultrasonic wave image regarding the x direction, the y direction and the z direction is structured. Among the time axis signal (z-directional signal) data 501 to 504, 501a represents a reflected ultrasonic wave signal from the front surface 400a of the sample 400, and 501b, a reflected ultrasonic wave signal from the rear face 400b. On the other hand, 501c in the time axis signal (z-directional signal) data 502 represents a reflected ultrasonic wave signal from a defect 401 within the sample 400.

This three-dimensional ultrasonic wave image is delivered to the display with defect determining unit 600, a three-dimensional ultrasonic wave image 601 of the sample 400 is displayed on a display unit or the like, and the internal defect 401 is revealed as an internal defect image 602.

To add, so that the airborne ultrasonic wave 204 emitted from the ultrasonic wave transmitting unit 200 may not come directly incident on the interferometric displacement sensor 100, obviously due consideration should be given to the arrangement of the two elements and to restraining of vibration.

The configuration and functions of the interferometric displacement sensor 100 in this embodiment will now be described with reference to FIG. 2 through FIG. 4. As shown in FIG. 2, the interferometric displacement sensor 100 comprises an optical interferometer 110 and an ultrasonic wave signal arithmetic processing unit 40. In the optical interferometer 110, a linearly polarized laser beam in a 90° direction emitted from the polarization maintaining fiber 2 is converted by a collimator 3 into a parallel beam 4 and further transmitted by a polarizing element 5, such as a Glan-Thompson prism, and a transmitted beam 6 is caused to be reflected by the prism mirror 7 and an nonpolarizing beam splitter 8 to be brought to incidence on a reference mirror 9.

Figure 3:
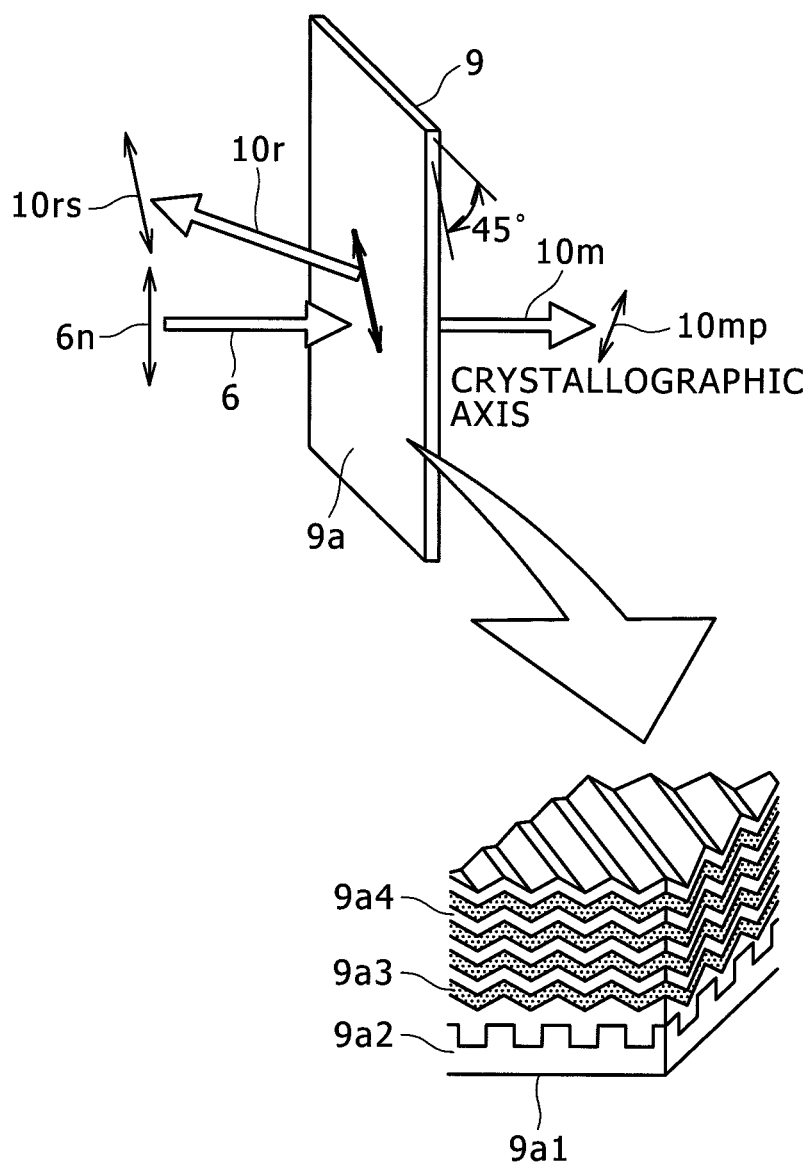
FIG. 3 is a perspective view showing the configuration and function of a reference mirror using a photonic crystal in the first embodiment of the invention.

As shown in FIG. 3, the reference mirror is composed of a photonic crystal 9a. The photonic crystal 9a, as shown in the magnified perspective view, is configured by forming 45°-directed line and space diffraction grating 9a2 on a synthetic quartz substrate 9a1, with which pitch is smaller than the wavelength of the incident light, and depositing dielectric thin films 9a3 and 9a4 differing from each other in refractive index over the grating substrate 9a1. By controlling the bias sputtering conditions at the time of depositing the dielectric thin films 9a3 and 9a4, the convexo-concave shape of the diffraction grating can be maintained in the sectional structure of the thin film layers as a convexo-concave shape of a triangular waveform to the uppermost layer along the direction of film thickness. Usable thin film materials include Si, $SiO_2$, $TiO_2$, $Ta_2O_5$ and $Nb_2O_5$. Such a diffraction grating-based multilayer thin film structure functions as a photonic crystal whose diffraction grating direction is the crystallographic axis direction (represented by a bold arrow), and is caused to exhibit birefringence property (optical anisotropy) by refraction and interference between the multiple layers of thin films, enabling the polarization and transmission/reflection characteristics of the incident light to be controlled. (Cf. the product catalog of Photonic Lattice, Inc. (in Japan)). The pitch and depth of the diffraction grating and the thickness of each thin film are controlled in consideration of the wavelength of the incident light and the desirable characteristics. Another major feature is that polarizing elements and waveplate elements differing in the direction of the crystallographic axis can be formed in an array over a single substrate by utilizing photolithography technique and film formation technique such as sputtering, which are used in semiconductor manufacturing process. In this embodiment, the photonic crystal 9a functions as a polarizing element. The direction of the diffraction grating (the direction of the crystallographic axis) is set at 45°, and the linearly polarized laser beam 6 in the 90° direction (denoted by 6n in the drawing) is incident on the reference mirror 9. In this case, S polarized component 10rs of the laser beam 6, whose polarization direction is the same as the direction of the crystallographic axis, is reflected by the surface of the photonic crystal 9a while the P polarized component 10mp orthogonal to the direction of the crystallographic axis is transmitted by the photonic crystal 9a. An S polarized component 10r reflected by the reference mirror 9 is used as a reference beam, and a P polarized beam 10m transmitted by the same is used as a probe beam. It is also possible to use, instead of the photonic crystal 9a, a grated polarizing element, such as a wire grid polarizer configured by forming a diffraction grating of a metallic material, such as Al, over a glass substrate.

The P polarized beam 10m transmitted by the reference mirror 9 is focused by a focusing lens 11 onto the excitation area where the reflected ultrasonic wave vibration 205 is caused on the surface of the sample 400 as a convergent beam 12. Thus, the focal position of the focusing lens 11 is coincident with the surface of the sample 400. A reflected beam from the excitation area again becomes a P polarized parallel beam 10m after being transmitted by the focusing lens 11, and is transmitted by the reference mirror 9. The S polarized component 10r (reference beam) reflected by the reference mirror 9 and the transmitted P polarized beam 10m are synthesized into an orthogonal polarized beams 14, which are transmitted by the nonpolarizing beam splitter 8.

This orthogonal polarized beams 14, after having passed an aperture 13 for removal of stray light, is divided into four channels of orthogonal polarized beams 16 by two quadrangular pyramidal prisms 15a and 15b. The applicable method of beam division is not limited to the use of such prisms, but diffraction optical elements or cube-shaped beam splitters can as well be used in combination. The two beams of each channel 16 interfere with additional phase shifts of 0, $\pi/2$, $\pi$ and $3\pi/2$ by passing through a phase shift element 17, resulting in the four channels of the phase-shifted interference beams 20.

Figure 4:
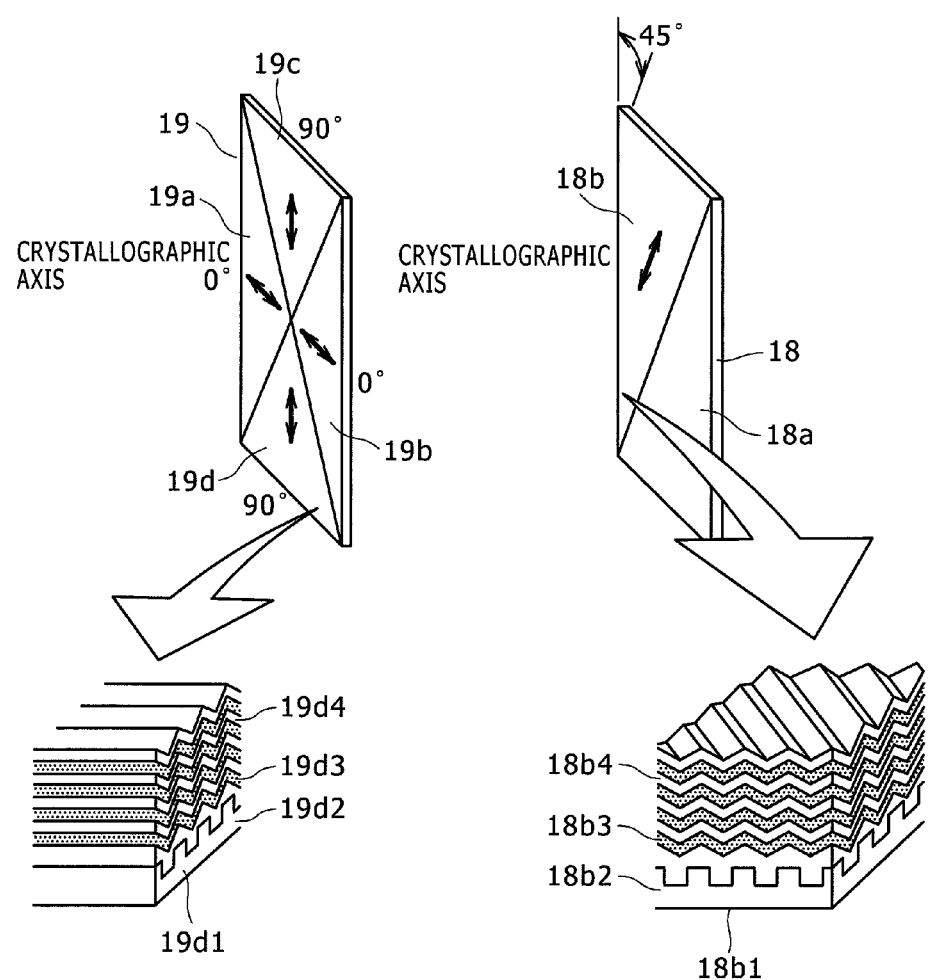
FIG. 4 is a perspective view showing the configuration of a phase shift element using a photonic crystal array in the first embodiment of the invention.

As shown in FIG. 4, the phase shift element 17 is formed of two photonic crystal arrays 18 and 19. The photonic crystal array 18 comprises two areas, the lower right half being formed of synthetic quartz 18a and the upper left half, of a photonic crystal 18b. The photonic crystal 18b, as shown in the magnified perspective view, is configured by forming 45°-directed line and space diffraction grating 18b2 on a synthetic quartz substrate 18b1, with which pitch is smaller than the wavelength of the incident light, and depositing dielectric thin films 18b3 and 18b4 differing from each other in refractive index over the grating substrate 9a1. The photonic crystal 18b functions as a ¼ wave plate, and a bold arrow represents the direction of its crystallographic axis. Thus, as shown in FIG. 2, the two channels of orthogonal polarized beams of the four channels of orthogonal polarized beams 16 are transmitted by the photonic crystal 18b, and then a phase difference of $\pi/2$ arises between orthogonal polarized components for each channel. On the other hand, the remaining two channels of orthogonal polarized beams are transmitted by the synthetic quartz 18a, and no phase difference arises between orthogonal polarized components for each channel.

The photonic crystal arrays 19, as shown in FIG. 4, comprises four areas, of which the left and right parts are configured of photonic crystals 19a and 19b having an 0° crystallographic axis direction (represented by a bold arrow) and the top and bottom parts are configured of photonic crystals 19c and 19d having an orthogonal 90° crystallographic axis direction (represented by a bold arrow). The photonic crystal of each area, to take up the photonic crystal 19d by way of example, is configured by forming 90°-directed line and space diffraction grating 19d2 on a synthetic quartz substrate 19d1, with which pitch is smaller than the wavelength of the incident light, and depositing dielectric thin films 19d3 and 19d4 differing from each other in refractive index over the grating substrate 9a1, as shown in the magnified perspective view. The same is true of the structure of the photonic crystals 19a, 19b and 19c. The four photonic crystals 19a, 19b, 19c and 19d function as polarizing elements, and a bold arrow represents the direction of its crystallographic axis. Thus, as shown in FIG. 2, the two channels of orthogonal polarized beams of the four channels of orthogonal polarized beams 16 are transmitted by the photonic crystals 19a and 19b, and then a phase difference of n arises between orthogonal polarized components for each channel. On the other hand, the remaining two channels of orthogonal polarized beams are transmitted by the photonic crystals 19c and 19d, and no phase difference arises between orthogonal polarized components for each channel. Finally, the two beams of each channel interfere each other.

Thus, the orthogonal polarized components of the four channels of orthogonal polarized beams 16, passing through the phase shift element 17 comprising the two photonic crystal arrays 18 and 19, interfere with additional phase shifts of 0, $\pi/2$, $\pi$ and $3\pi/2$, resulting in the four channels of the phase-shifted interference beams 20. The four channels of phase-shifted interference beams 20 are, by being transmitted by four imaging lenses 21, received as a focused beams 22 on the photo acceptance faces of four photoelectric conversion elements 23, which are photodiodes or the like, and, after being amplified by an amplifier 24, outputted as four channels of phase-shifted interference signals 31a, 31b, 31c and 31d.

As is evident from FIG. 2, the focal positions of the four imaging lenses 21 are coincident with the photo acceptance faces of the photoelectric conversion elements 23. Therefore, the surface of the sample 400 and the photo acceptance faces of the photoelectric conversion elements 23 are in a relationship of conjugation, namely a relationship of image formation. For this reason, even if the surface of the sample 400 is inclined or has minute convexes and concaves, or the surface of the sample 400 is rough, a reflected beam from the surface is accurately condensed and received by the photo acceptance faces of the photoelectric conversion elements 23, and stable phase-shifted interference signals 31a, 31b, 31c and 31d can be obtained.

The four phase-shifted interference signals 31a, 31b, 31c and 31d are respectively represented by Equations (1) to (4):

$$I_a = I_m + I_r + 2(I_m \cdot I_r)^{1/2}\cos(4\pi nD/\lambda) \quad (1)$$

$$I_b = I_m + I_r + 2(I_m \cdot I_r)^{1/2}\cos(4\pi nD/\lambda + \pi/2) \quad (2)$$
$$= I_m + I_r - 2(I_m \cdot I_r)^{1/2}\sin(4\pi nD/\lambda)$$

$$I_c = I_m + I_r + 2(I_m \cdot I_r)^{1/2}\cos(4\pi nD/\lambda + \pi) \quad (3)$$
$$= I_m + I_r - 2(I_m \cdot I_r)^{1/2}\cos(4\pi nD/\lambda)$$

$$I_d = I_m + I_r + 2(I_m \cdot I_r)^{1/2}\cos(4\pi nD/\lambda + 3\pi/2) \quad (4)$$
$$= I_m + I_r + 2(I_m \cdot I_r)^{1/2}\sin(4\pi nD/\lambda)$$

where $I_m$ is the detected intensity of a probe beam 10m; $I_r$, the detected intensity of a reference beam 10r; n, the refractive index of air; D, the amplitude of the reflected ultrasonic wave vibration 205 excited on the surface of the sample 400; and $\lambda$, the wavelength of the laser beam 4. In the ultrasonic wave signal arithmetic processing unit 40, the amplitude D of the reflected ultrasonic wave vibration 205 excited on the surface of the sample 400 is calculated according to Equation (5), and inputted to the signal controller-processor 300 as the ultrasonic wave signal 51.

$$D=(\lambda/4\pi n)\tan^{-1}\{(I_d-I_b)/(I_a-I_c)\} \quad (5)$$

As is seen from FIG. 2, two beams including a probe beam 10m with which the surface of the sample 400 is irradiated and a reference beam 10r are emitted from the laser source unit 1 and comes incident on the interferometric displacement sensor 100 travel exactly the same optical path until they reach the reference mirror 9 and are further received by the four photoelectric conversion elements 23 from the reference mirror 9. Thus, it is the configuration of a common-path type interferometer. Therefore, even if the temperature distribution or the refractive index distribution due to air fluctuations or mechanical vibration occur on the optical paths, these external disturbances equally impact both beams, and therefore the impacts of these external disturbances are cancelled out when both beams interfere, leaving the interference beams free from the effects of such disturbances. As an exception, on the optical path between the reference mirror 9 and the sample 400, only the probe beam 10m and its focusing beam 12 are present, but, if the spacing between the reference mirror 9 and the focusing lens 11 is kept at not more than 1 mm and the focal distance of the focusing lens 11 is set at approximately 5 mm or less, the spacing between the reference mirror 9 and the sample 400 can be set to no more than 8 mm even with an approximately 2 mm thickness of the focusing lens 11 taken into account. The influence of external distances in such a minute gap could be ignored. Also, intensity fluctuations of the laser beam itself would be fluctuations for the detected intensity $I_m$ of the probe beam and for the detected intensity $I_r$ of the reference beam in Equations (1) to (4), but they can be canceled by subtraction processing and division processing in Equation (5) by the ultrasonic wave signal arithmetic processing unit 40.

Further in the interferometric displacement sensor 100 of this embodiment, as the four channels of orthogonal polarized beams are generated by a simple configuration and four channels of phase-shifted interference beams are generated and received by the arrayed photonic crystals spatially in parallel, the number of optical components required is drastically reduced compared with conventional phase-shifting interferometers, resulting in an advantage that the interferometric displacement sensor can be significantly reduced in size. More specifically, the dimensions of the optical interferometer 110 can be reduced to around 20(W)×50(L)×14(H) mm. Furthermore, as the our phase-shifted interference beams travel optical paths which are close to each other, even if the external disturbances such as the temperature distribution, humidity distribution, atmospheric pressure distribution, density distribution, and air flow variations due to air fluctuations occur on the optical paths, their impacts can be kept to the minimum. As the interferometric displacement sensor 100 can be reduced in size in such a way, its combination with the ultrasonic wave transmitting unit 200 to scan over the sample 400 in the x direction and the y direction is facilitated.

Figure 5:
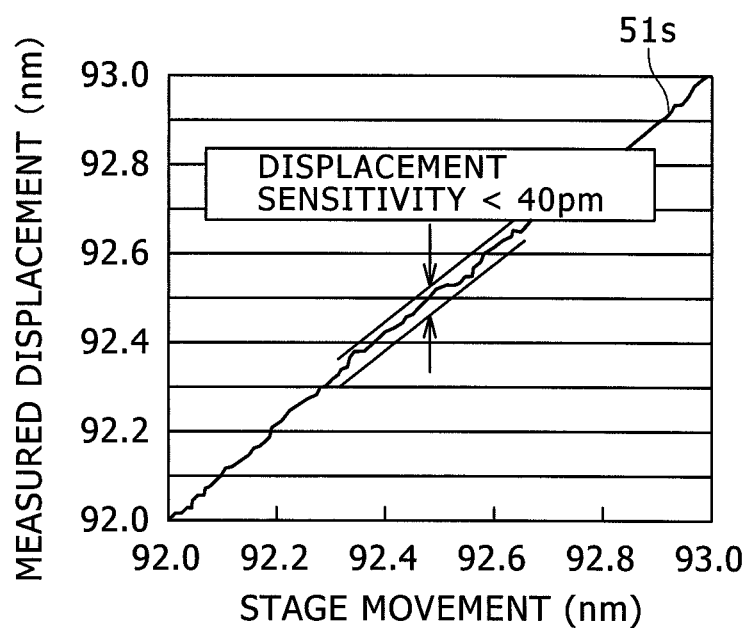
FIG. 5 is a graph showing the displacement sensitivity of the interferometric displacement sensor in the first embodiment of the invention.

The results of measurement of minute displacements with a trial product of the interferometric displacement sensor 100 are shown in FIG. 5. The object of measurement was a piezoelectric element stage. The horizontal axis in the graph represents the stage movement when the piezoelectric element stage was scanned over a range of 1 nm, and the vertical axis, the displacements measured by the interferometric displacement sensor 100. From the variation extent of the measured displacement signal 51s, it is known that the displacement sensitivity of the interferometric displacement sensor 100 is smaller than 40 picometers (pm), revealing a sensitivity 10 times or even more as high as that of conventional optical interferometers. Because of what has been said, this interferometric displacement sensor 100 can stably measure the displacement of the object or the amplitude of the ultrasonic wave vibration in the order of picometers without requiring precise control of such environmental factors as temperature, humidity, atmospheric pressure, density and acoustic vibration. Thus in the ultrasonic wave transmitting unit 200, though the equipment of the oscillator with the acoustic matching layer restrains the difference in acoustic impedance between the oscillator and air and thereby enables ultrasonic waves to be emitted into the air at a high propagation efficiency, this airborne ultrasonic wave is significantly attenuated when it comes incident on the sample 400. As a result, the amplitude of the ultrasonic wave vibration reflected or transmitted by an internal defect and arising on the surface of the sample 400 has attenuated to a sub-nanometer level or even below. For this reason, no conventional optical interferometer was able to detect this minute ultrasonic wave vibration that is excited by airborne ultrasonic waves on the sample surface. Unlike that, as shown in FIG. 5, the interferometric displacement sensor 100 of this embodiment has a displacement sensitivity to 40 pm or even small, and has succeeded for the first time in detecting a minute ultrasonic wave vibration whose amplitude is in the order of picometers that is excited by airborne ultrasonic waves on the sample surface.

Although the interferometric displacement sensor 100 is arranged on the same side as the ultrasonic wave transmitting unit 200 relative to the sample 400 in this embodiment to detect an ultrasonic wave vibration reflected by an internal defect, it is also permissible to arrange the interferometric displacement sensor 100 on the reverse side to the ultrasonic wave transmitting unit 200 to detect an ultrasonic wave vibration transmitted by an internal defect.

As shown in FIG. 1 through FIG. 5, this embodiment achieves high-sensitivity detection of ultrasonic wave vibrations with a minute amplitude in the order of picometers excited by airborne ultrasonic waves on the sample surface, without being affected by the influence of any external disturbance, and even if the surface of the sample is inclined or has minute convexes and concaves or the surface of the sample is rough, stable non-contact non-destructive detection of any internal defect in the sample is made possible.

Second Embodiment

Figure 6:
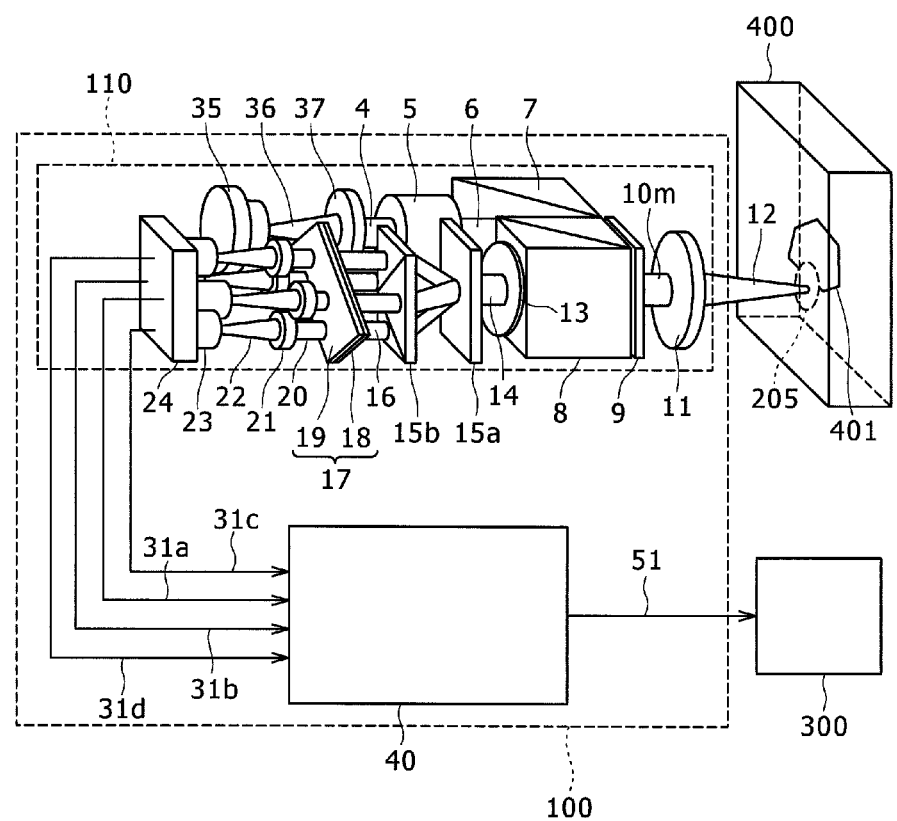
FIG. 6 is a combination of a perspective view and a block diagram showing the configuration of the interferometric displacement sensor in a second embodiment of the invention.

A second embodiment of the present invention will be described below with reference to FIG. 6. FIG. 6 shows the interferometric displacement sensor 100 in an internal defect inspection apparatus of this embodiment.

In the first embodiment, the linearly polarized laser beam emitted from the laser source unit 1 is guided by the polarization maintaining fiber 2 to the interferometric displacement sensor 100. Unlike that, in the interferometric displacement sensor 100 of this embodiment, as shown in FIG. 6, in place of the laser source unit 1 and the polarization maintaining fiber 2, a small laser diode 35, which may be a semiconductor laser or the like as the laser source is built into the optical interferometer 110. Therefore, the use of the laser diode 35 serves to dispense with beam guidance with a fiber and enables the laser source to be directly built into the optical interferometer, resulting in a reduction in the overall device size. A 90°-directed linearly polarized laser beam 36 emitted from the laser diode 35 is converted by a collimating lens 37 into the parallel beam 4, which is further transmitted by the polarizing element 5, such as a Glan-Thompson prism, and the transmitted beam 6 is reflected by the prism mirror 7 and the nonpolarizing beam splitter 8 to be brought to incidence on the reference mirror 9. As the configurations and functions of the ensuing elements and those of the internal defect inspection apparatus are exactly the same as the respective counterparts in the first embodiment in FIG. 1 and FIG. 2, except the laser source unit 1 and the polarization maintaining fiber 2, their description will be dispensed with.

As shown in FIG. 6, this embodiment can achieve high-sensitivity detection of ultrasonic wave vibrations with a minute amplitude in the order of picometers excited by airborne ultrasonic waves on the sample surface, without being affected by the influence of any external disturbance. Therefore, even if the surface of the sample is inclined or has minute convexes and concaves or the surface of the sample is rough, stable non-contact non-destructive detection of any internal defect in the sample is made possible. Furthermore, as this embodiment has a laser diode built into the interferometric displacement sensor 100, no laser source unit is required, and the overall size of the internal defect inspection apparatus is reduced. Moreover, it is made even easier to scan the surface of the sample 400 in the x direction and the y direction in combination with the ultrasonic wave transmitting unit 200.

Third Embodiment

Figure 7:
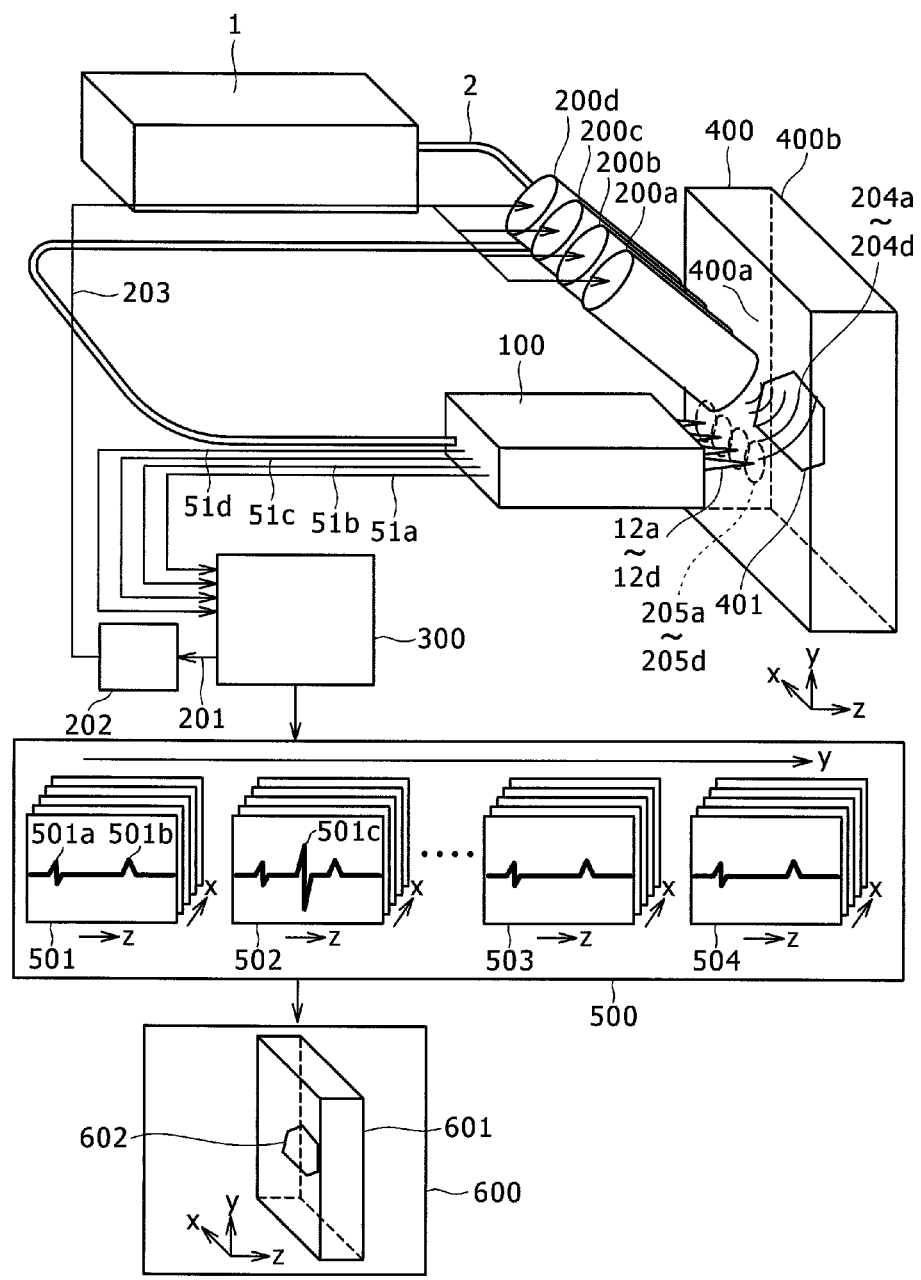
FIG. 7 is a combination of a perspective view and a block diagram showing the overall configuration of an internal defect inspection apparatus in a third embodiment of the invention.

A third embodiment of the present invention will now be described with reference to FIG. 7. FIG. 7 shows the overall configuration of an internal defect inspection apparatus in this embodiment.

The first embodiment has one each of the ultrasonic wave transmitting unit 200 that emits an airborne ultrasonic wave and the interferometric displacement sensor 100 that detects an ultrasonic wave vibration reflected or transmitted from within a sample, and a three-dimensional ultrasonic wave image is obtained by scanning the unit 200 and the sensor 100 in the x direction and the y direction. Unlike that, as shown in FIG. 7, this embodiment has a plurality of ultrasonic wave transmitting units 200a, 200b, 200c and 200d arrayed in the x direction, and they emit a plurality of airborne ultrasonic waves 204a, 204b, 204c and 204d either simultaneously or in a time series. On the other hand, an interferometric displacement sensor 100 is arranged at a corresponding position, with which a plurality of optical interferometers 110 and ultrasonic wave signal arithmetic processing units 40 are built into it. From the interferometric displacement sensor 100, a plurality of probe beams 12a, 12b, 12c and 12d arrayed in the x direction are focused by the respective excitation areas where a plurality of ultrasonic wave vibrations 205a, 205b, 205c and 205d are generated on the surface of the sample 400, and a phase change accompanying the ultrasonic wave vibrations occurs on their reflected beams. This phase change is detected by the interferometric displacement sensor 100 as an amplitude change of an interference beams, and a plurality of ultrasonic wave signals 51a, 51b, 51c and 51d are outputted and delivered to the three-dimensional image constructing unit 500 via the signal controller-processor 300.

In the three-dimensional image constructing unit 500, a three-dimensional ultrasonic wave image representing the internal structure of the sample 400 is configured by using the ultrasonic wave image sets 501 to 504 obtained by scanning the ultrasonic wave transmitting units 200a, 200b, 200c and 200d and the interferometric displacement sensor 100 in the y direction in the air at a certain distance above the sample 400. As the functions of the ensuing elements are exactly the same as the respective counterparts in the first embodiment, their description will be dispensed with. Incidentally, it is also possible to combine the second embodiment with this embodiment.

In this embodiment, obviously internal defects can be detected with even higher resolution by increasing the number of ultrasonic wave transmitters and optical interferometers. It is also possible to replace the plurality of ultrasonic wave transmitters with an ultrasonic wave transmitter that emits a linear airborne ultrasonic wave.

As shown in FIG. 7, this embodiment can achieve high-sensitivity detection of ultrasonic wave vibrations with a minute amplitude in the order of picometers excited by airborne ultrasonic waves on the sample surface, without being affected by the influence of any external disturbance. Therefore, even if the surface of the sample is inclined or has minute convexes and concaves or the surface of the sample is rough, stable non-contact non-destructive detection of any internal defect in the sample is made possible. Furthermore, as this embodiment can obtain a three-dimensional ultrasonic wave image of the sample by scanning the ultrasonic wave transmitters and the interferometric displacement sensor only in the y direction in the air at a certain distance above the sample, the scanning mechanism can be simplified, and the time taken for internal defect inspection can be reduced at the same time.

Fourth Embodiment

Figure 8:
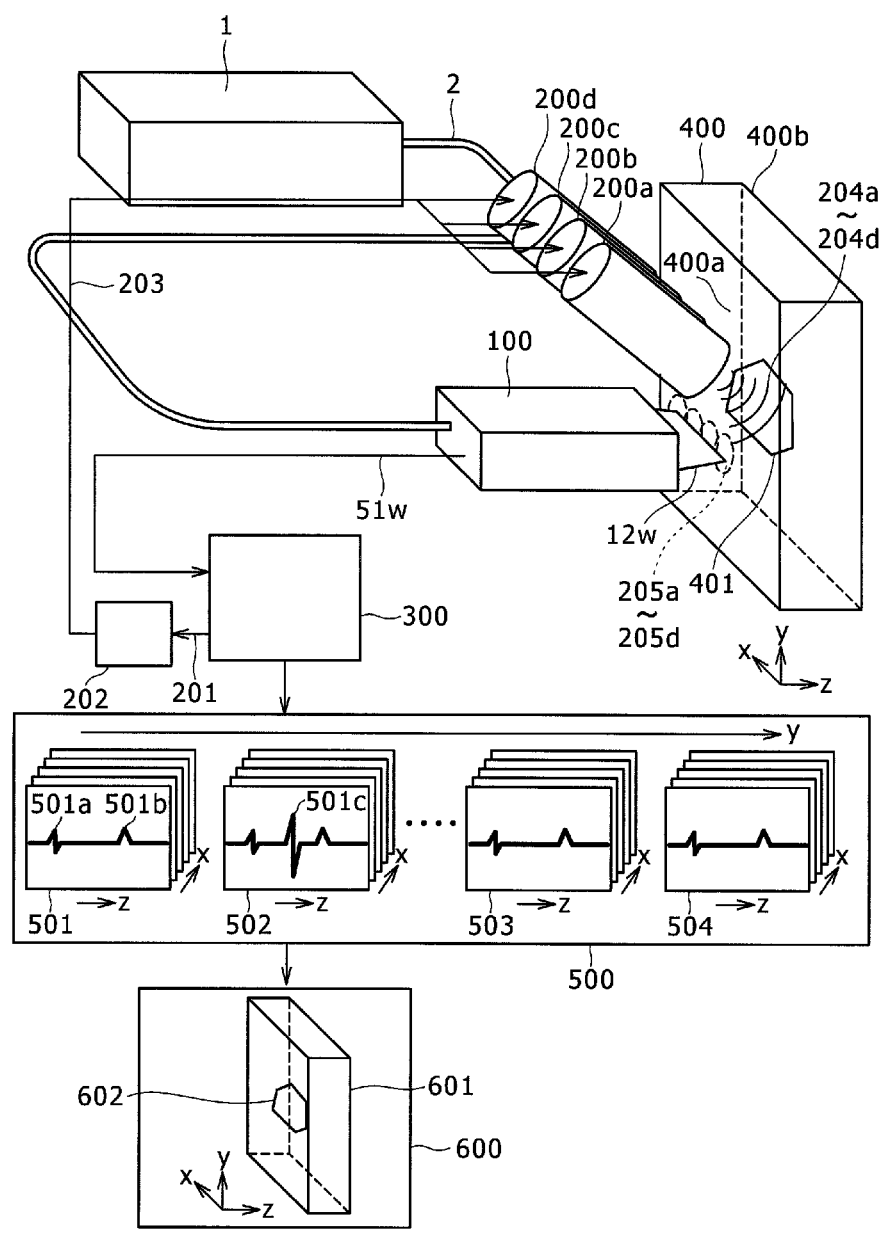
FIG. 8 is a combination of a perspective view and a block diagram showing the overall configuration of an internal defect inspection apparatus in a fourth embodiment of the invention.

A fourth embodiment of the present invention will now be described with reference to FIG. 8 through FIG. 11. FIG. 8 shows the overall configuration of an internal defect inspection apparatus in this embodiment.

In this embodiment, as in the third embodiment, a plurality of ultrasonic wave transmitting units 200a, 200b, 200c and 200d are arrayed in the x direction, and emit a plurality of airborne ultrasonic waves 204a, 204b, 204c and 204d either simultaneously or in a time series. On the other hand, from the interferometric displacement sensor 100, a linear probe beam 12w along the x direction is emitted to irradiate the respective excitation areas where a plurality of ultrasonic wave vibrations 205a, 205b, 205c and 205d are generated on the surface of the sample 400, and a phase change accompanying the ultrasonic wave vibrations occurs on its reflected beam. This phase change is detected by the interferometric displacement sensor 100 as an amplitude change of an interference beam, and a plurality of ultrasonic wave signals 51w are outputted and delivered to the three-dimensional image constructing unit 500 via the signal controller-processor 300.

In the three-dimensional image constructing unit 500, a three-dimensional ultrasonic wave image representing the internal structure of the sample 400 is configured by using the ultrasonic wave image sets 501 to 504 obtained by scanning the ultrasonic wave transmitting units 200a, 200b, 200c and 200d and the interferometric displacement sensor 100 in the y direction in the air at a certain distance above the sample 400. As the functions of the ensuing elements are exactly the same as the respective counterparts in the first embodiment, their description will be dispensed with.

Figure 9:
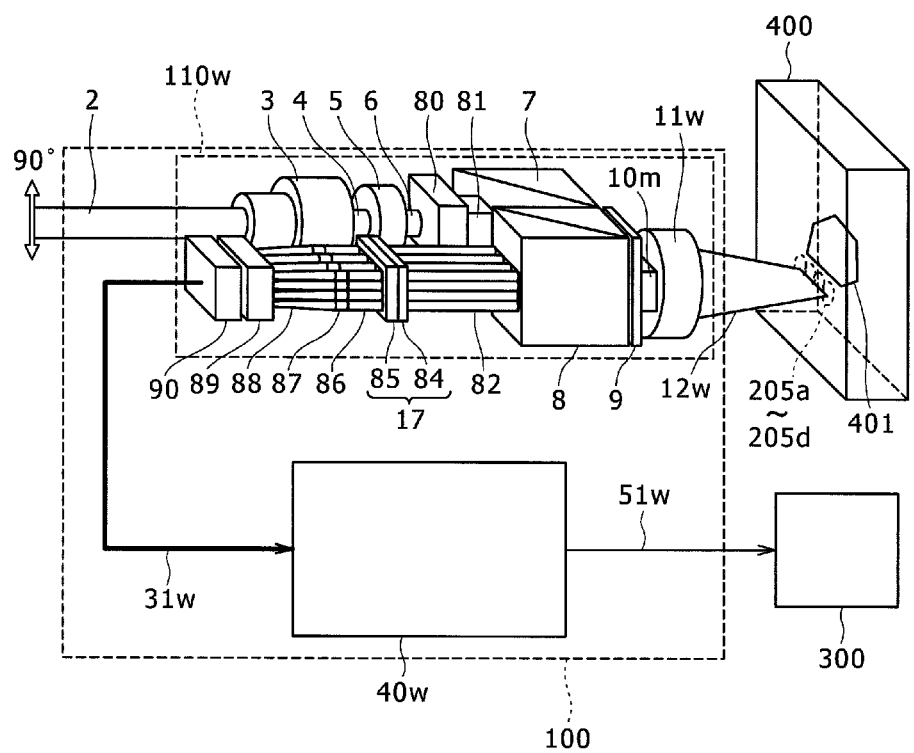
FIG. 9 is a combination of a perspective view and a block diagram showing the configuration of an interferometric displacement sensor in the fourth embodiment of the invention.

The configuration and functions of the interferometric displacement sensor 100 of this embodiment will be described with reference to FIG. 9 through FIG. 11. As shown in FIG. 9, the interferometric displacement sensor 100 comprises the optical interferometer 110w that emits a linear probe beam 12w and the ultrasonic wave signal arithmetic processing unit 40w. In the optical interferometer 110w, a 90°-directed linearly polarized laser beam emitted from the polarization maintaining fiber 2 is converted into the parallel beam 4 by the collimator 3 and further transmitted by the polarizing element 5, such as a Glan-Thompson prism, and the transmitted beam 6 is converted into rectangular beam 81 by a beam shaping element 80, such as a diffraction optical element or a hologram element, or an anamorphic prism pair. The rectangular beam 81 is reflected by the prism mirror 7 and the nonpolarizing beam splitter 8 and brought to incidence on the reference mirror 9.

The reference mirror 9, as shown in FIG. 3, is composed of the photonic crystal 9a. The photonic crystal 9a, as shown in the magnified perspective view, is configured by forming 45°-directed line and space diffraction grating 9a2 on a synthetic quartz substrate 9a1, with which pitch is smaller than the wavelength of the incident light, and depositing dielectric thin films 9a3 and 9a4 differing from each other in refractive index over the grating substrate 9a1. By controlling the bias sputtering conditions at the time of depositing the dielectric thin films 9a3 and 9a4, the convexo-concave shape of the diffraction grating can be maintained in the sectional structure of the thin film layers as a convexo-concave shape of a triangular waveform to the uppermost layer along the direction of film thickness. Usable thin film materials include Si, $SiO_2$, $TiO_2$, $Ta_2O_5$ and $Nb_2O_5$. Such a diffraction grating-based multilayer thin film structure functions as a photonic crystal whose diffraction grating direction is the crystallographic axis direction (represented by a bold arrow), and is caused to exhibit birefringence property (optical anisotropy) by refraction and interference between the multiple layers of thin films, enabling the polarization and transmission/reflection characteristics of the incident light to be controlled. Also, polarizing elements and wave-plate elements differing in the direction of the crystallographic axis can be formed in an array over a single substrate by utilizing photolithography technique and film formation technique such as sputtering, which are used in semiconductor manufacturing process. In this embodiment, the photonic crystal 9a functions as a polarizing element. The direction of the diffraction grating (the direction of the crystallographic axis) is set at 45°, and the linearly polarized laser beam 6 in the 90° direction (denoted by 6n in the drawing) is incident on the reference mirror 9. In this case, S polarized component 10rs of the laser beam 6, whose polarization direction is the same as the direction of the crystallographic axis, is reflected by the surface of the photonic crystal 9a while the P polarized component lamp orthogonal to the direction of the crystallographic axis is transmitted by the photonic crystal 9a. The S polarized component 10r reflected by the reference mirror 9 is used as a reference beam, and the P polarized beam 10m transmitted by the same is used as a probe beam. It is also possible to use, instead of the photonic crystal 9a, a grated polarizing element, such as a wire grid polarizer, configured by forming a diffraction grating of a metallic material, such as Al, over a glass substrate.

The rectangular P polarized beam 10m transmitted by the reference mirror 9 is focused by a focusing lens 11w, and is linearly focused as the convergent beam 12w along the respective excitation areas where the plurality of ultrasonic wave vibrations 205a, 205b, 205c and 205d is caused on the surface of the sample 400. Thus, the focal position of the focusing lens 11w is coincident with the surface of the sample 400. A reflected beam from the excitation areas again becomes a P polarized rectangular beam 10m after being transmitted by the focusing lens 11, and is transmitted by the reference mirror 9. The S rectangular polarized component 10r (reference beam) reflected by the reference mirror 9 and the rectangular P polarized beam 10m transmitted by the reference mirror 9 are synthesized into a rectangular orthogonal polarized beams 82, and are transmitted by the nonpolarizing beam splitter 8.

These rectangular orthogonal polarized beams 82 interfere with additional phase shifts of 0, π/2, π and 3π/2 by passing through a phase shift element 83, resulting in the four channels of the phase-shifted interference beams 86 divided in a direction orthogonal to the longitudinal direction of the linear convergent beam 12w.

Figure 10:
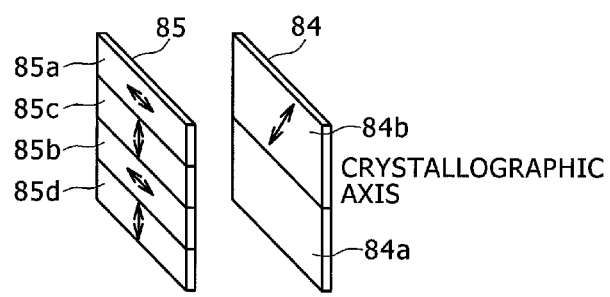
FIG. 10 is a perspective view showing the configuration of a phase shift element using a photonic crystal array in the fourth embodiment of the invention.

The phase shift element 83 is configured of two photonic crystal arrays 84 and 85 as shown in FIG. 10. The photonic crystal array 84 is divided into two areas in a direction orthogonal to the longitudinal direction of a linear convergent spot 12w, with the lower half formed of synthetic quartz 84a and the upper half, of a photonic crystal 84b. As the configuration and principle of the photonic crystal 84b are the same as those of the reference mirror 9, their description will be dispensed with. The photonic crystal 84b functions as a ¼ wave plate, and a bold arrow in the 45° direction represents its crystallographic axis direction. Thus, as shown in FIG. 9, the upper half of the rectangular orthogonal polarized beams 82 are transmitted by the photonic crystal 84b, and then a phase difference, of π/2 arises between orthogonal polarized components. On the other hand, the lower half of the rectangular orthogonal polarized beams 82 are transmitted by the synthetic quartz 84a, and no phase difference arises between orthogonal polarized components.

The photonic crystal array 85 is divided into four segments in a direction orthogonal to the longitudinal direction of the linear convergent spot 12w as shown in FIG. 10, and the photonic crystals 85a and 85b having a 0° crystallographic axis direction and photonic crystals 85c and 85d having an orthogonal 90° crystallographic axis direction alternate each other. The photonic crystals 85a, 85b, 85c and 85d function as polarizing elements, and the bold arrow indicates their crystallographic axis direction. Thus, as shown in FIG. 9, orthogonal polarized beams transmitted by the photonic crystals 85a and 85b interfere each other with additional phase shifts of π0 between orthogonal polarized components. On the other hand, orthogonal polarized beams transmitted by the photonic crystals 85c and 85d interfere each other without additional phase shifts between orthogonal polarized components.

Thus, the orthogonal polarized components in a direction orthogonal to the longitudinal direction of the rectangular orthogonal polarized beams 82, transmitted by the phase shift element 83 comprising two photonic crystal arrays 84 and 85, interfere with additional phase shifts of 0, $\pi/2$, $\pi$ and $3\pi/2$. As a result, the four channels of phase-shifted interference beams 86 are generated in a direction orthogonal to the longitudinal direction of the linear convergent spot 12w and conjugate in the longitudinal direction of the linear convergent spot 12w. The phase-shifted interference beams 86, as shown in FIG. 9, are focused and received by the photo acceptance faces of divided type photoelectric conversion elements 89, such as a photodiode array, comprising N pixels×4 light receiving areas as N×4 convergent beams 88 by N×4 lens arrays 87 matching the longitudinal direction of the linear convergent spot 12w and the four areas of the phase shift element 83 and, after being amplified by an amplifier 90, outputted as N×4 phase-shifted interference signals 31w. As shown in FIG. 11, light receiving areas 89a, 89b and 89c, 89d respectively match the photonic crystals 85a, 85b, 85c and 85d of the photonic crystal array 85 shown in FIG. 10. Further, as is evident from FIG. 9, the focal positions of the lens arrays 87 are coincident with the light receiving areas of the photoelectric conversion elements 89. Therefore, the surface of the sample 400 and the photo acceptance faces of photoelectric conversion elements 89 are in a relationship of conjugation, namely a relationship of image formation via the focusing lens 11w and the lens arrays 87. For this reason, even if the surface of the sample 400 is inclined or has minute convexes and concaves or the surface of the sample 400 is rough, reflected beams from the surface are accurately focused and received by the photo acceptance faces of photoelectric conversion elements 89 to give the stable phase-shifted interference signals 31w.

The four phase-shifted interference signals 31w corresponding to an N pixel are given by Equations (1) to (4) as in the first embodiment, and the ultrasonic wave signal arithmetic processing unit 402 calculates the amplitude D of each of the reflected ultrasonic wave vibrations 205a through 205d excited on the surface of the sample 400 for each of the N pixels in accordance with Equation (5). The amplitudes are inputted to the signal controller-processor 300 as N ultrasonic wave signals 51w.

As shown in FIG. 8 and FIG. 9, this embodiment can achieve high-sensitivity detection of ultrasonic wave vibrations with a minute amplitude in the order of picometers excited by airborne ultrasonic waves on the sample surface, without being affected by the influence of any external disturbance, and, even if the surface of the sample is inclined or has minute convexes and concaves or the surface of the sample is rough, stable non-contact non-destructive detection of any internal defect in the sample is made possible. Furthermore, as this embodiment can obtain a three-dimensional ultrasonic wave image of the sample by scanning the ultrasonic wave transmitters and the interferometric displacement sensor only in the y direction in the air at a certain distance above the sample, the scanning mechanism can be simplified, and the time taken for internal defect inspection can be reduced at the same time.

Further, the third embodiment uses a plurality of optical interferometers to simultaneously detect ultrasonic wave signals from a plurality of points on the sample, and accordingly it has the advantages of simplifying the scanning mechanism configuration and at the same time reducing the time for internal defect inspection. On the other hand, however, the configuration of its interferometric displacement sensor is made complex. Unlike that, this embodiment requires only one optical interferometer by virtue of the use of rectangular beams, and therefore its interferometric displacement sensor configuration is simplified, enabling the cost to be reduced, while retaining the advantages of the third embodiment.

In these four embodiments of the invention it is also permissible to use, instead of the photonic crystal array, a grated polarizing element, such as a wire grid polarizer, configured by forming a diffraction grating of a metallic material, such as Al, over a glass substrate.

Advantageous Effects of First Through Fourth Embodiments

As hitherto described, the first through fourth embodiments of the invention can achieve high-sensitivity detection of ultrasonic wave vibrations with a minute amplitude in the order of picometers excited by airborne ultrasonic waves on the sample surface, without being affected by the influence of any external disturbance, and even if the surface of the sample is inclined or has minute convexes and concaves or the surface of the sample is rough, stable non-contact non-destructive detection of any internal defect in the sample is made possible. As a result, internal defects such as exfoliations, cracks or voids caused in a rolled steel sheet, composite steel sheet, casting, ceramic substrate or the like the sample, can be detected in a non-contact non-destructive way.

While the invention accomplished by the present inventor has been described in specific terms with reference to embodiments thereof, the invention is not limited to these embodiments, but can obviously be modified in various manners without deviating from the essentials thereof.

What is claimed is:

1. An internal defect inspection method whereby an ultrasonic wave is emitted from an ultrasonic wave transmitter toward a sample to propagate within the sample to produce an ultrasonic wave vibration proximate a surface of the sample, the ultrasonic wave vibration is detected by an imaging type common-path interferometer as an interference signal, an ultrasonic wave signal is obtained from the interference signal, and any defect within the sample is detected from the ultrasonic wave signal.

2. The internal defect inspection method according to claim 1, wherein:
the imaging type common-path interferometer emits a laser beam, causes a reference mirror to reflect part of the laser beam, causes the sample to reflect the laser beam transmitted by the reference mirror, and detects the laser beams reflected by the reference mirror and the sample and subjected to polarizing interference in a state of being given a phase shift from a phase shift element.

3. The internal defect inspection method according to claim 2, wherein:
the imaging type common-path interferometer focuses onto the surface of the sample the laser beam by the reference mirror with a focusing lens and causes the phase-shifted laser beam from the phase shift element to be focused by an imaging lens.

4. The internal defect inspection method according to claim 1, wherein:
the imaging type common-path interferometer guides a laser beam emitted from a laser source with a polarization maintaining fiber.

5. The internal defect inspection method according to claim 2, wherein:
the imaging type common-path interferometer converts a laser beam emitted from a laser diode into a parallel beam with a collimating lens and brings the parallel beam into incidence on the reference mirror.

6. The internal defect inspection method according to claim 1, wherein:
ultrasonic waves are emitted from a plurality of ultrasonic wave transmitters into the air and ultrasonic wave vibrations from within the sample are detected with a plurality of imaging type common-path interferometers on a surface of the sample.

7. The internal defect inspection method according to claim 6, wherein:
the laser beam is converted into a rectangular beam by a shaping element and brought to incidence on the reference mirror.

8. An internal defect inspection apparatus comprising:
an ultrasonic wave transmitter that emits an ultrasonic wave into the air and causes the ultrasonic wave to propagate within a sample to produce an ultrasonic wave vibration proximate a surface of the sample;
an imaging type common-path interferometer that detects the ultrasonic wave vibration from the surface of the sample as an interference signal; and
an ultrasonic wave signal detecting device that detects an ultrasonic wave signal from the interference signal detected by the imaging type common-path interferometer.

9. The internal defect inspection apparatus according to claim 8, wherein:
the imaging type common-path interferometer is provided with a laser source to emit a laser beam, a reference mirror that reflects a part of and transmits another part of the laser beam, and a phase shift element that gives a phase shift to the laser beam.

10. The internal defect inspection apparatus according to claim 9, wherein:
the imaging type common-path interferometer is provided with a focusing lens that focuses the laser beam transmitted by the reference mirror onto the surface of the sample and an imaging lens that focuses the phase-shifted laser beam from the phase shift element.

11. The internal defect inspection apparatus according to claim 9, wherein:
the reference mirror is configured of a grated polarizing element.

12. The internal defect inspection apparatus according to claim 9, wherein:
the phase shift element is configured of a grated polarizing element.

13. The internal defect inspection apparatus according to claim 9, wherein:
the reference mirror is configured of a photonic crystal.

14. The internal defect inspection apparatus according to claim 9, wherein:
the phase shift element is configured of a photonic crystal.

* * * * *